United States Patent [19]

McVicker

[11] Patent Number: 5,492,133
[45] Date of Patent: Feb. 20, 1996

[54] IMPROVED FLEXIBLE FASTENING STRAP

[75] Inventor: Henry J. McVicker, Chatham, N.J.

[73] Assignee: Aircast, Inc., Summit, N.J.

[21] Appl. No.: 131,030

[22] Filed: Oct. 4, 1993

Related U.S. Application Data

[63] Continuation of Ser. No. 839,475, Feb. 19, 1992, abandoned.

[51] Int. Cl.[6] .................................................. A61F 5/00
[52] U.S. Cl. .................... 128/876; 602/27; 24/442; 128/DIG. 15
[58] Field of Search .................................. 602/5, 16, 20, 602/21, 23–29, 65, 75; 128/DIG. 15, 876–878, 882; 482/79, 105; 24/442, 306, 16 PB, 17 AP; 606/201, 203, 204

[56] References Cited

U.S. PATENT DOCUMENTS

| | | | |
|---|---|---|---|
| Re. 33,395 | 10/1990 | Peters | 602/27 |
| 3,674,023 | 7/1972 | Mann | 602/65 |
| 4,280,489 | 7/1981 | Johnson, Jr. | |
| 4,693,239 | 9/1987 | Clover, Jr. | 602/27 |
| 4,878,274 | 11/1989 | Patricy | 24/306 |
| 4,977,891 | 12/1990 | Grim | 602/27 |
| 4,999,888 | 3/1991 | Miller | 24/442 X |
| 5,007,416 | 4/1991 | Burns et al. | 602/27 |
| 5,026,089 | 6/1991 | Grimmonpie | 24/306 X |
| 5,038,762 | 8/1991 | Hess et al. | 602/27 |
| 5,069,202 | 12/1991 | Prock | 602/27 |
| 5,167,050 | 12/1992 | Korsen | 24/306 X |

*Primary Examiner*—Linda C. Dvorak
*Attorney, Agent, or Firm*—Jones, Day, Reavis & Pogue

[57] ABSTRACT

An improved ankle support system including first and second support side walls and attaching straps which have an elongated hook portion pivotally attached to the side wall support and which has an elongated loop portion integrally formed with the hook portion and having a width wider than the loop portion such that when the strap is wrapped around the leg, the loop portion entirely covers the hook portion.

3 Claims, 5 Drawing Sheets

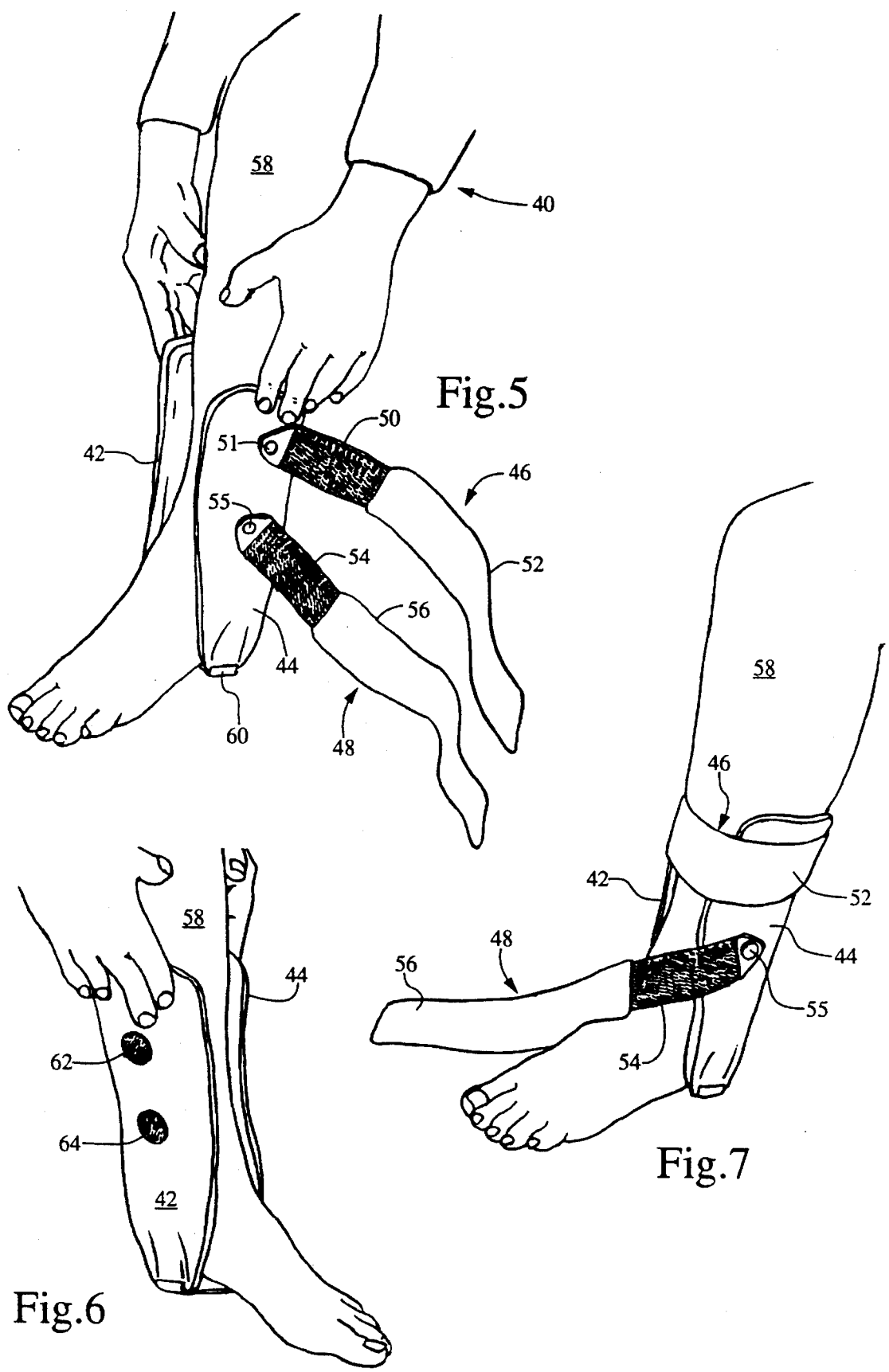

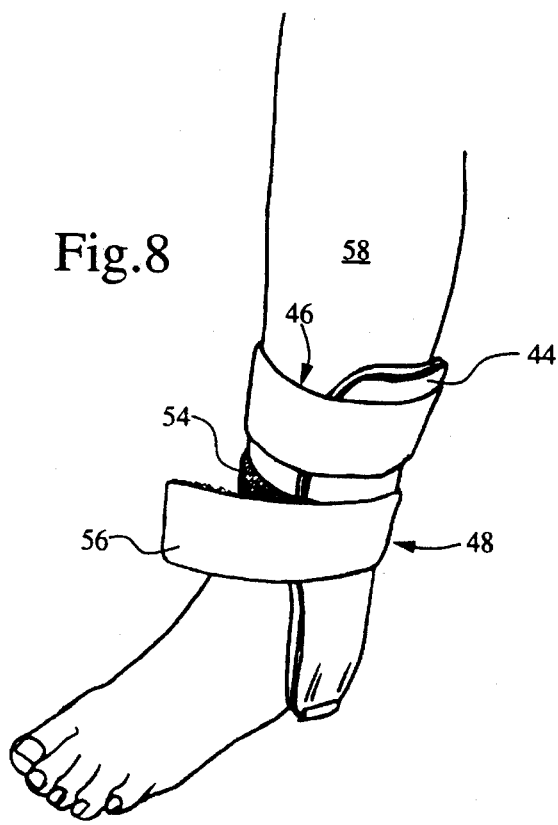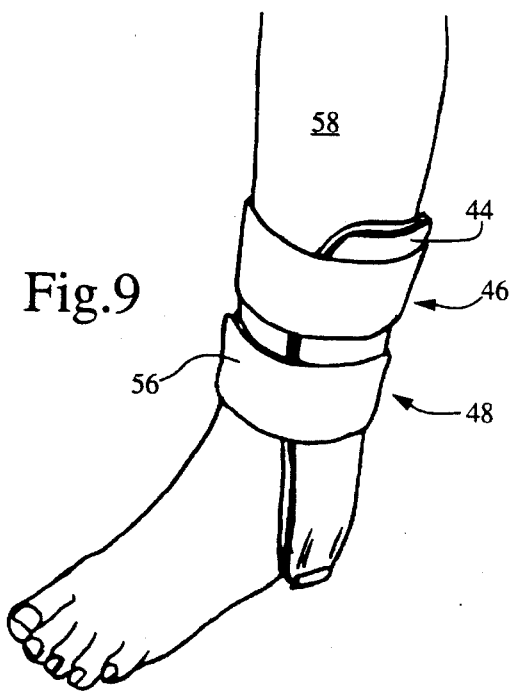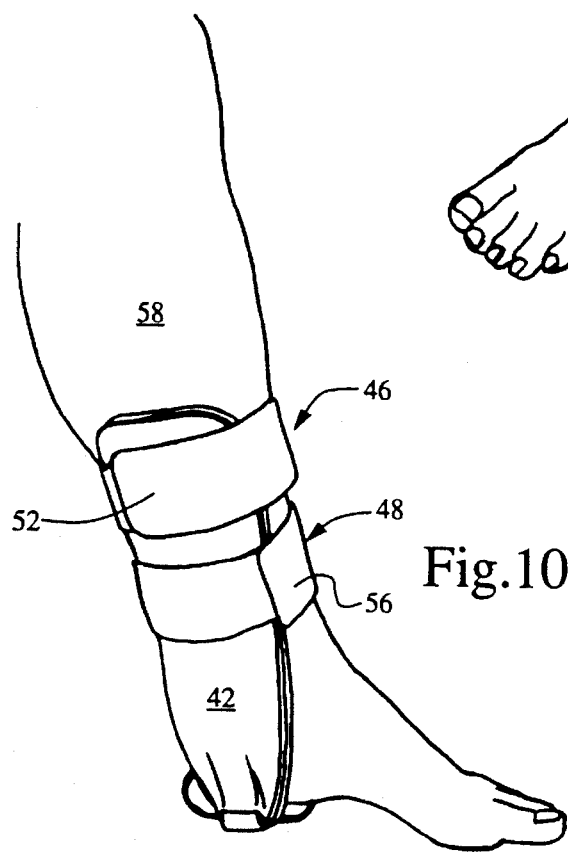

IMPROVED FLEXIBLE FASTENING STRAP

This is a continuation of application Ser. No. 07/839,475 filed on Feb. 19, 1992, now abandoned.

FIELD OF THE INVENTION

The present invention relates to leg braces in general and in particular to an ankle brace having side wall supports with attachment straps swivelly attached thereto. The attachment straps each have hooks and loops thereon for attaching the strap to itself and is so constructed that the hooks are fully covered when the straps are attached to prevent the hooks from engaging articles such as clothing that comes in contact therewith.

BACKGROUND OF THE INVENTION

An ankle brace has been disclosed in commonly assigned U.S. Pat. No. 4,280,489 in which a generally U-shaped stirrup member has a base portion and a pair of opposed side wall portions attached to the base portion. When the stirrup member is fitted about the lower extremity of the leg, the side wall portions engage the lateral and medial portions of the ankle. A plurality of fastener straps are provided to maintain the side wall portions of the stirrup member snugly fitted about the lower leg above the ankle. The fastener straps each is a two-inch wide strip of pressure sensitive hook Velcro welded to a length of loop Velcro. The hook portion is adhesively attached to the outer shell of the side wall portion with the upper strap at an angle so as to spiral and lay flat against the tapered leg. Because of the adhesive attachment of the hook portion of the strap to the outer wall of the shell, the angle is fixed. Further, in order to secure the outer end of the strap once it is wrapped around the wall supports and the leg, a circular area of hook material must be adhesively attached to the outside of the loop portion of the strap such that the outer end of the loop portion, after encircling the leg, will engage the circular hook portion to securely hold it.

Thus a disadvantage of the prior art device is that the angle at which the straps is adhered to the side wall portion is fixed. The strap must circle the leg at an angle, thus leaving a portion of the attachment hooks exposed. This exposed portion of the attachment hooks engages other material that comes in the vicinity thereof, such as trousers, ladies' stockings and the like. Further, because the attached hook portion is short, the additional circular area of hook material must be placed on the outside of the loop portion of the strap at a distance from the attached hook portion on the side wall portion. This extra hook material requires a more difficult process in forming the straps because it must be added on the outer side thereof. Further, because the hook material is adhesively adhered to the side wall portion, the straps have to be wrapped around the leg at the preset angle.

The present invention overcomes the disadvantages of the prior art by providing an improved ankle brace attaching straps pivotally attached to the side wall portions so that their alignment to the leg can conform to the individual rather than being preset. Further, the orientation in a clockwise or counterclockwise direction can be changed to individual preference. Both straps may encircle the leg in a first direction or a second direction or one of the straps can encircle the leg in one direction and the other strap can encircle the leg in the other direction.

Further, the attaching straps of the present invention are made of 1½ strip of plastic hook Velcro welded to a length of 2" loop material. Because the hook portion is of molded plastic, its end can be reformed by ultrasonic energy into a flat section simultaneously with its welding to the loop. The now flattened plastic can then by die cut to the finished shape and a hole appears therein reinforced for attachment by a rivet to the side wall portion. This arrangement has several advantages over the prior art. Because the straps are swiveled, their alignment to the leg can conform to the individual rather than being preset. Further, because the hook portion is nonadhesively secured to the stirrup, it can be longer, extending well past the edge of the wall support. This makes possible the use of the narrower material without sacrificing strength. This narrow strip of material makes possible the total covering of the hook by the loop. Finally, cost savings are significant. Pressure-sensitive hook and loop material is extremely expensive and the present invention decreases its use. Because the hook is longer, the separate circular area of hook material which tethers the loose end is eliminated. The entire process of strap manufacture is thus simplified.

Thus it is an object of the present invention to provide an improved ankle brace which has side wall support to which at least one of the supports is pivotally attached an attachment strap.

It is also an object of the present invention to provide an improved ankle brace in which the attachment strap has a first portion pivotally attached to the side wall support and having a first width and a second portion attached to the first portion and having a larger width such that when the strap is wrapped around and encircles the leg, it will entirely cover the exposed hook portion of the strap.

SUMMARY OF THE INVENTION

Thus the present invention relates to an improved ankle brace for use in immobilizing the ankle against inversion and eversion while permitting plantarflexion and dorsiflexion thereof and including a pair of spaced apart side wall support portions, the improvement comprising flexible fastening means having a first attachment portion pivotally attached to at least one of the side wall supports and a second leg encircling portion for wrapping around the leg, the pivotal attachment enabling the second leg encircling portion to conform to the leg of the individual and encircle the leg in either direction, and the first attachment portion having means for engaging the leg encircling portion such that the side wall portions are held in abutting relationship against the sides of the ankle.

BRIEF DESCRIPTION OF THE DRAWINGS

These and other objects of the present invention will be more fully disclosed in conjunction with the following detailed specification and the drawings in which like numerals represent like elements and in which:

FIG. 5 is an isometric view of the novel ankle support system with the side wall supports being placed against the ankles;

FIG. 6 is a view of the side wall supports from the inside of the left leg before the straps are fastened thereto;

FIG. 7 is an isometric view of the right side of the leg illustrating one of the novel straps having been wrapped around the leg and the side wall supports and the other strap in the position ready to be wrapped around the leg and the side wall supports;

FIG. 8 is an isometric representation of the system on the leg with the first strap fastened and the second strap almost wrapped completely around the leg;

FIG. 9 is an isometric view of the right side of the leg illustrating the system when it has been completely attached to the ankle for support; and FIG. 10 is an isometric view of the left side of the leg illustrating the completed system attached to the ankle.

DETAILED DESCRIPTION OF THE DRAWINGS

Figure 1:
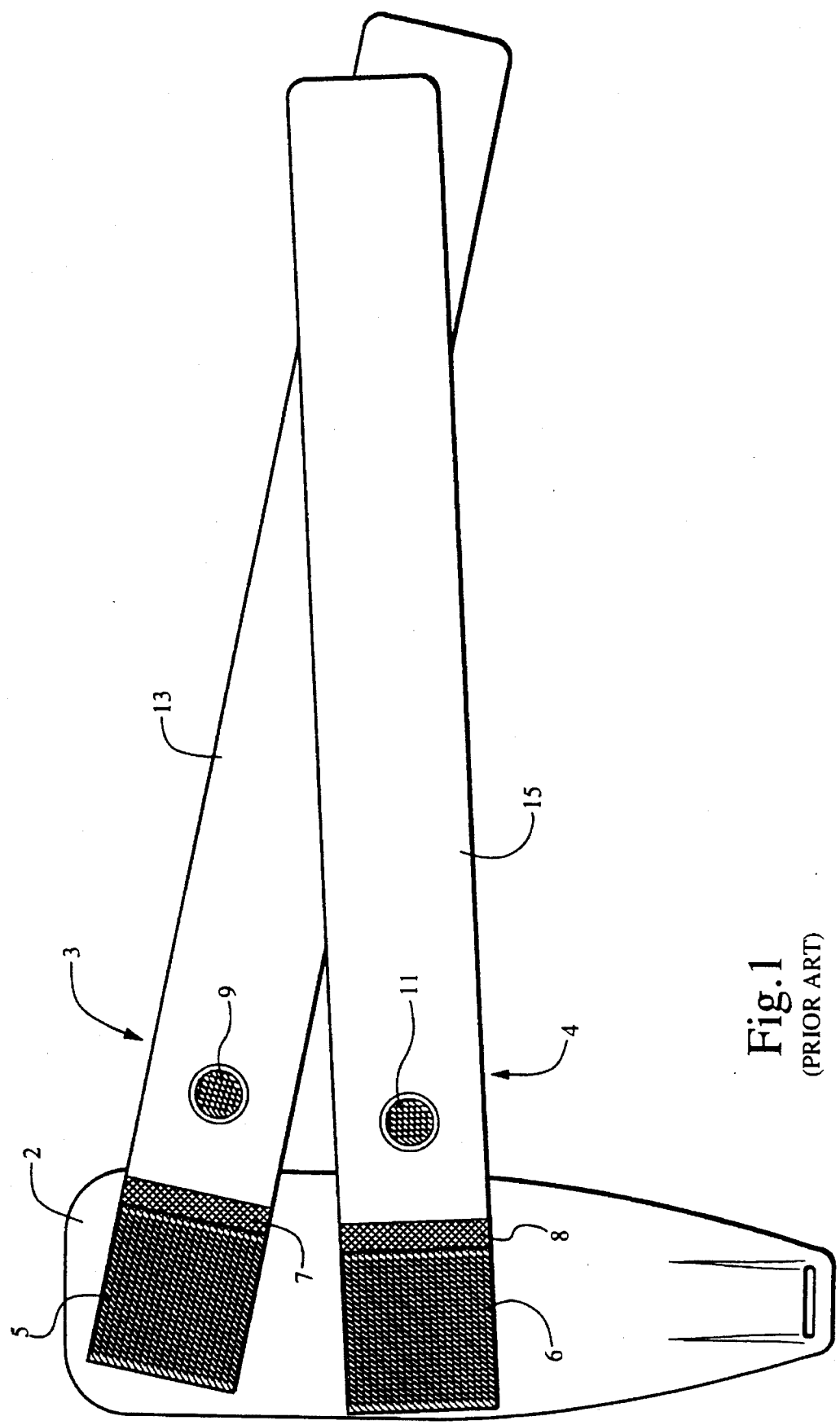
FIG. 1 is a schematic representation of an ankle brace of the prior art.

FIG. 1 is a plan view of a prior art ankle support system for one side of the leg. As can be seen in FIG. 1, the side wall support 2 has attached thereto straps 3 and 4 for wrapping around the leg, corresponding support 2 on the other side of the leg and back to the original side to hold the supports 2 on each side of the leg in place. Strap 3 has a hook portion 5 that is adhesively attached in a well-known manner to the side wall support 2. It will be noted that the strap 3 is attached at an angle to the horizontal to side wall support 2. It is welded to a length 13 of loop Velcro at the area 7. The weld 7 is made in any well-known manner to attach sections 5 and 13. The upper strap 3 is attached to the side wall support 2 at an angle so as to spiral and lay flat against the tapered leg. Because of the adhesive attachment of the hook portion 5 to the side wall 2, the angle is fixed and cannot be varied. As strap 13 is used to encircle the leg and the two side wall supports 2, it exposes a portion of the hook area 5 thus enabling the exposed portion to contact adjacent clothing such as ladies' stockings. Further, a "coin" or circular area 9 of hook material must be located as indicated to tether the loose end of the strap 13 as it extends beyond the hook portion 5.

The second strap 4 is attached substantially perpendicular to the long axis of the side wall support 2. It is approximately one inch shorter than the upper strap 3. It also has a hook portion 6 that is attached in any well-known manner to the side wall support 2 such as, for example, only by adhesive. A length 15 of the loop material is welded at area 8 to the hook area 6. As the loop portion 15 of the strap is wrapped around the leg and the side wall support 2 on the other side of the leg, it can adhere to hook material 6. However, because the outer end extends beyond hook area 6, a small "coin" or circular area 11 of hook material is placed on the strip of loop material 15. The straps are required to be of the length shown, approximately 16.125" for the short strap 4 and approximately 17.125" for the long strap 3, so that they can accommodate various size legs. Again, the coin or circular area 11 of hook material tethers the outer end of the loop portion 15 of the strap 4.

Thus with the design illustrated in FIG. 1 of the prior art, their alignment to the leg cannot conform to the individual and are preset. Further, the orientation, clockwise or counterclockwise encircling of the leg, cannot be changed to individual preference. Further, the hook portion is adhesively secured to the side wall supports, its length is limited and cannot extend past the edge of the side wall support 2. This causes a portion of the upper hook section 5 to be exposed, enabling it to snag adjacent materials such as the ladies' stockings. Further, it is expensive in construction to add the circular hook area 9 and 11 on the two straps 3 and 4 and the process of strap manufacture is more complicated because they must be added.

Figure 2:
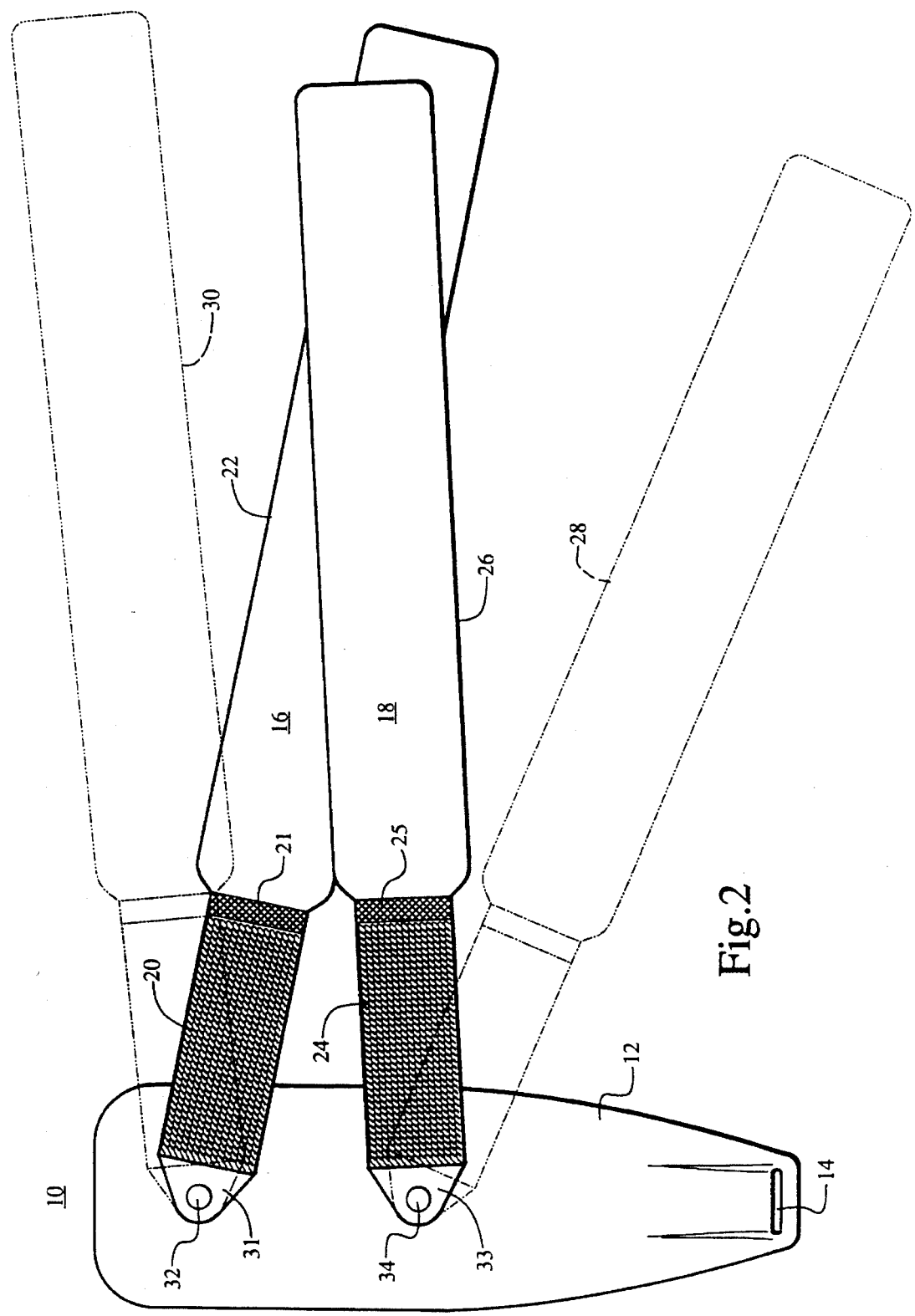
FIG. 2 is a plan view of the novel improved ankle brace of the present invention.

The improved ankle brace system is illustrated in FIG. 2. The system 10 comprises side wall support 12 which has an opening 14 on the bottom thereof to allow a flexible strap to connect it to an adjacent support on the opposite side of the leg. An upper strap 16 is pivotally attached to the side wall support 12 at 32 while a lower strap 18 is pivotally attached to the side wall support 12 at 34. Upper strap 16 consists of an elongated hook portion 20 which, as is well known in the art, is made of molded plastic, has its inner end 31 reformed by ultrasonic energy into a flat section. Further, it is welded at 21 to the loop portion 22 of the strap 16.

In like manner, the lower, shorter strap 18 is attached to the side wall support 12 by the pivot arrangement 34. Again, the short strap 18 has an elongated hook portion 25 which has the inner end 33 thereof reformed by ultrasonic energy into a flat section as is well known in the art. The orifice for the pivot 34 is formed in the inner section 33. The hook section 24 is ultrasonically welded to the loop portion 26 in the area 25 but can be attached in any well-known manner. It will be noted first that upper strap 16 can be swiveled or pivoted about pivot point 32 in a 360° range of motion, one of which positions is illustrated by the numeral 30 designating the phantom lines. In like manner, the lower, shorter strap 18 can be pivoted 360° about pivot point 34 to any position therein such as illustrated by position 28 in phantom lines.

It will also be noted that the hook portions 20 and 24 of straps 16 and 18 have a width which is narrower than the width of the loop portions 22 and 26 of the straps 16 and 18. Because the straps are swiveled at 32 and 34, their alignment to the leg can conform to the individual rather than being preset. Further, the orientation, either clockwise or counterclockwise, can be changed to individual preference.

Further, because the hook portions 20 and 24 are not adhesively secured to the side wall support 12, they can be longer than in the prior art and extend well past the outer edge of the side wall portion 12. This makes possible the use of a narrower strip than in the prior art without sacrificing strength. Further, because the outer portions 22 and 26 of the straps 16 and 18 are wider than the width of the hook portions 20 and 24, when they wrap around the leg, they can totally cover the hook material 20 and 24 with the loop material 22 and 26. This then will eliminate the problem of the hook material engaging other materials such as the ladies' stockings.

Figure 3A:
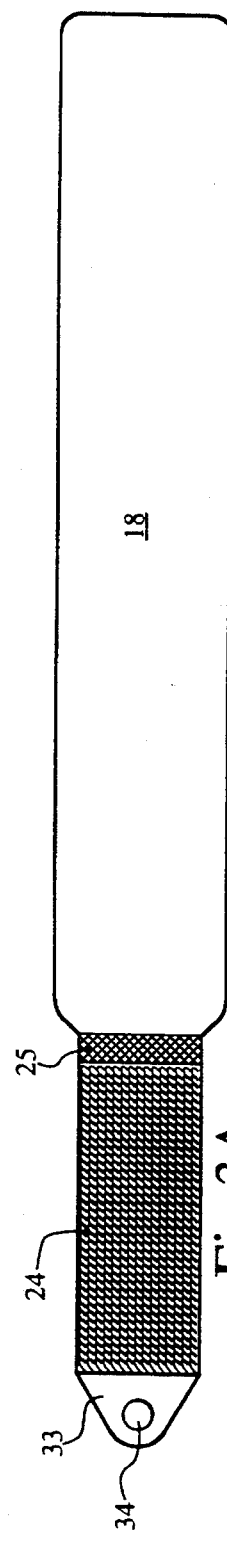
FIG. 3a is a plan view of one of the novel fastening straps of the present invention as compared to the prior art strap illustrated in FIG. 3b.
Figure 3B:
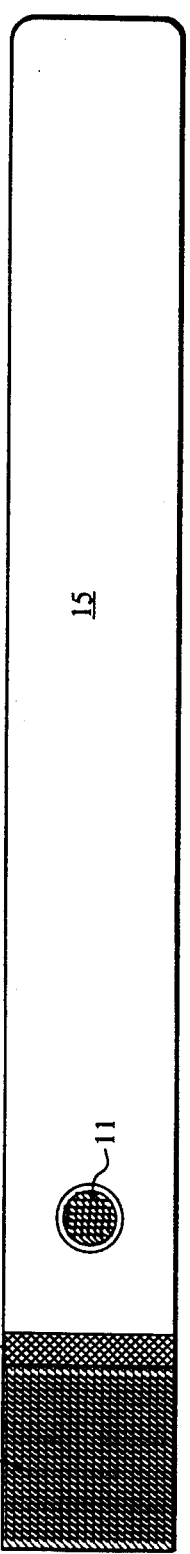

Finally, the cost savings of the device in FIG. 2 over the device in FIG. 1 is significant. Pressure-sensitive Velcro is extremely expensive and the present design reduces the amount required or eliminates its use. Because the hook sections 20 and 24 are longer, the separate coin of hook material 9 and 11 illustrated in FIG. 1 is eliminated. Thus the entire process of strap manufacture is simplified. FIG. 3a is a plan view of the new lower strap 18 which is the shorter strap. It has a total length of 16.938" with the length of hook material 24 being approximately 4.825" and the loop material 18 being approximately 12.25" including the weld area 25. The width of the hook material 24 is 1½" while the width of the loop material is 2". As can be seen in FIG. 3b, the old strap was 16.125" in length with the length of the hook material 6 being 2.375" and the length of the loop material 15 being 14" including the welded area 8. The entire strap including both the hook section 6 and the loop section 15 has a width of 2". The coin or circular area of hook material 11 has a radius of 0.438".

Figure 4A:
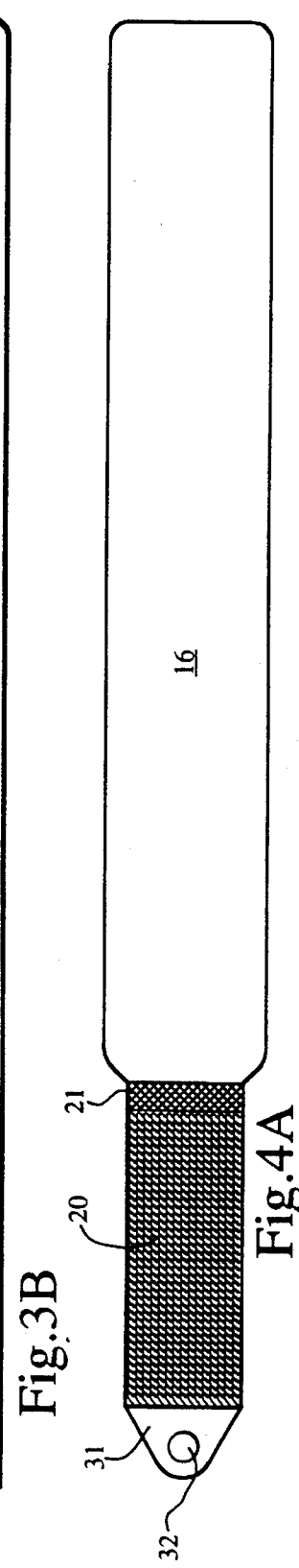
FIG. 4a is a plan view of the other of the novel ankle straps of the present invention as compared to the prior art strap illustrated in FIG. 4b.
Figure 4B:
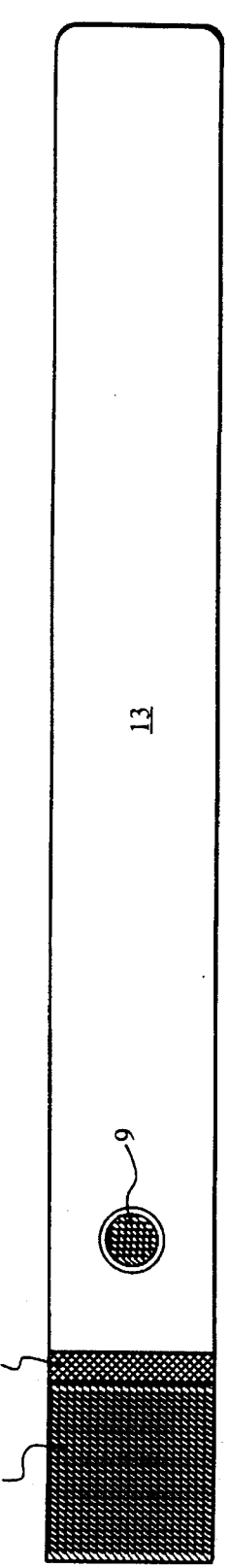

In FIG. 4a, the new upper strap 16 has the total length of 17.894" including the flattened area 31 which contains the orifice 32. The loop portion 20 is 1½" wide and approximately 4.815" in length. The loop material portion 16 is 2" in width and approximately 13.25" in length including the welded area 21. The old strap shown in FIG. 4b is 2" wide, 17.125" in length total. The length of the hook material area 5 is 2.125" and the coin of hook material 9 has a radius of 0.438".

FIG. 5 is an isometric view illustrating a person generally designated by the numeral 40 placing the novel system on a leg 58. The two side wall supports 42 and 44 are joined at the base by a flexible strap 60 as is well known in the art and support wall 42 is on one side of the leg and wall 44 is on the other side of the leg. Upper strap 46 has the hook portion 50 and the loop portion 52 pivotally attached to wall portion 44 at pivot point 51. Lower strap 48 has the hook portion 54 and loop portion 56 and is pivotally attached to the side wall portion 44 at 55. FIG. 6 illustrates the side wall supports 42 and 44 from the other side of the leg. As can be seen in FIG. 6, circular hook areas 62 and 64 are attached to side wall support 42 in any well-known manner such as by adhesive or may be integrally formed therewith as disclosed in commonly assigned copending U.S. patent application Ser. No. 655,343, filed Mar. 6, 1991 and entitled "Method for Injection-Molding an Orthopedic Device and Product of the Method".

In FIG. 7 the upper strap 46 has been wrapped around the leg and the two side wall supports 42 and 44. The lower strap 48 with its hook portion 54 and loop portion 56 is ready to be wrapped around the leg 58 and the side wall portions 42 and 44. It will be noted because of the swivels 51 and 55 that the straps 46 and 48 may be encircled about the leg either clockwise or counterclockwise as desired.

FIG. 8 illustrates the system with the upper strap 46 completely encircling the leg and the side wall portions 42 and 44 with the lower strap 48 having the outer end 56 ready to be attached to and covering the hook portion 54 thereof. FIG. 9 illustrates the system when it is completely in place on the leg. Note that none of the Velcro portions 54 or 50 are visible. However, in the case of need, it is still possible to angle either or both of the straps 46 and 48 at an angle around the leg in a spiral fashion because of the swivel mounted straps.

FIG. 10 is a view of the leg 58 from the inside of the leg illustrating how the straps encircle the leg and the side wall supports 42 and 44 and entirely cover the Velcro hooks.

Thus there has been disclosed a novel improved ankle support system in which the two straps that are attached to the support walls are pivotally attached thereto so that they can be swiveled to any particular alignment with the leg and thus the alignment to the leg can conform to the individual instead of being preset as in the prior art. Further, as stated earlier, either a clockwise or counterclockwise orientation can be used to suit individual preference.

Further, because the hook portion is not adhesively secured to the side wall portions, they are longer and extend longer than the prior art sections of hook material and extend well past the edge of the support members. This makes possible the use of a narrower piece of hook material without sacrificing strength. This narrower hook material makes possible the total covering of the hook material by the loop material section of the strap. Further, the cost saving is significant because less pressure sensitive Velcro hook material is used and it is very expensive. No need for a separate circular or coin area of hook material on the loop material is required. The entire process of strap manufacture is thus simplified.

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

I claim:

1. A flexible strap containing both hook and loop releasable fastening elements and that is capable of attaching to itself and for securement to and for holding in place an underlying object, the flexible strap comprising:

a first side opposed to a second side;

an elongated, hook-containing, strap portion of unitary molded plastic, a plurality of hooks on said hook-containing, strap portion contained on said first side of said strap, and said hook-containing strap portion having first and second ends;

an integral reinforced flat section forming part of said first end of said hook-containing strap portion;

an opening in said integral reinforced flat section for receiving means which pivotally attaches said flexible strap to the underlying object;

an elongated, loop-containing, strap portion having opposed first and second ends, a plurality of loops on said loop-containing, strap portion contained on said second side of said strap;

said second end of said hook-containing strap portion being fixedly secured to one end of said loop-containing strap portion and said plurality of hooks on said hook-containing strap portion not overlying said plurality of loops on said loop-containing, strap portion when formed; such that, when said flexible strap is placed about an object, the loop-containing portion will overlap and be releasably affixed to said hook-containing portion.

2. The flexible strap set forth in claim 1, wherein said hook-containing strap portion is narrower in width than said loop-containing strap portion thereby permitting said hook portion to be completely covered by the overlapping loop portion without leaving any exposed hooks.

3. The strap set forth in claim 2, wherein said hook-containing strap portion is about 4.8 inches long, and 1½" inches wide, and said loop-containing portion is about 2" wide.

* * * * *